United States Patent [19]

Cerri et al.

[11] Patent Number: 5,705,662
[45] Date of Patent: Jan. 6, 1998

[54] 17-(3-IMINO-2-ALKYLPROPENYL)-5β, 14β-ANDROSTANE DERIVATIVES ACTIVE ON THE CARDIOVASCULAR SYSTEM, PROCESSES FOR THEIR PREPARATION AND PHARMACEUTICAL COMPOSITIONS CONTAINING SAME

[75] Inventors: Alberto Cerri, Gessate; Giuseppe Bianchi, Milan; Patrizia Ferrari, Varese; Piero Melloni, Bresso; Maria Luisa Quadri, Cernusco, all of Italy

[73] Assignee: Sigma-Tau Industrie Farmaceutiche Riunite S.p.A., Rome, Italy

[21] Appl. No.: 559,291

[22] Filed: Nov. 15, 1995

[30] Foreign Application Priority Data

Nov. 29, 1994 [DE] Germany .................. 44 42 486.8

[51] Int. Cl.$^6$ .................. C07J 9/00; A01N 45/00
[52] U.S. Cl. .................. 552/548; 552/553; 514/169; 514/182
[58] Field of Search .................. 552/548, 553; 514/169, 182

[56] References Cited

U.S. PATENT DOCUMENTS 5,324,719  6/1994  Frigerio et al. .
5,444,055  8/1995  Cerri et al. .

Primary Examiner—Gary Geist
Assistant Examiner—Deborah D. Carr
Attorney, Agent, or Firm—Oblon, Spivak, McClelland, Maier & Neustadt, P.C.

[57] ABSTRACT

New 17-[3-imino-2-alkyl propenyl]-14β-hydroxy-5β-androstane derivatives active on the cardiovascular system by inhibiting Na+,K+-ATPase, a process for their preparation, and to pharmaceutical compositions for the treatment of cardiovascular disorders, such as heart failure and hypertension.

19 Claims, No Drawings

17-(3-IMINO-2-ALKYLPROPENYL)-5β, 14β-ANDROSTANE DERIVATIVES ACTIVE ON THE CARDIOVASCULAR SYSTEM, PROCESSES FOR THEIR PREPARATION AND PHARMACEUTICAL COMPOSITIONS CONTAINING SAME

The present invention relates to new 17-(3-imino-2-alkylpropenyl)-14β-hydroxy-5β-androstane derivatives active on the cardiovascular system, to a process for their preparation and to pharmaceutical compositions containing same for the treatment of cardiovascular disorders, such as heart failure and hypertension.

The known 17β-guanidinoiminomethyl-5β-androstane-3β,14β-diol and 17-guanidinoimino-5β-androstane-3β,14β-diol are reported to be weak inhibitors of Na$^+$,K$^+$-ATPase and weak positive inotropic agents (Gelbart A. and Thomas R., *J. Med. Chem.*, 1978, 21, 284; Schönfeld W. and Repke K., *Quant. Struct. -Act. Relat.*, 1988, 7, 160). Other 17-hydroxyminomethyl-5β,14β-androstane derivatives (DE 4,227,605; filing date Aug. 20, 1992) and hydrazono-5β, 14β-androstane derivatives (DE 4,227,626: filing date Aug. 20, 1992) are reported to inhibit Na$^+$,K$^+$-ATPase.

The compounds of the present invention have general formula (I):

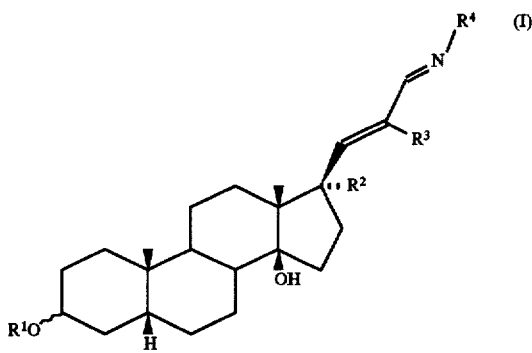

wherein:
the symbol ⁓ means α or β configuration:
the double bonds are in the E configuration;
R$^1$ represents hydrogen. C2–C4 alkyl unsubstituted or substituted by NR$^5$R$^6$ wherein
  R$^5$, R$^6$ which may be the same or different, represent hydrogen, C1–C4 alkyl or R$^5$ and R$^6$ may form, taken together with the nitrogen atom, a five- or six-membered saturated heterocyclic ring optionally containing one or more further heteroatoms selected from oxygen and nitrogen;
R$^2$ represents hydrogen or hydroxy;
R$^3$ represents methyl, ethyl or n-propyl;
R$^4$ represents NHC(=N⁓R$^7$)NR$^8$R$^9$ or OR$^{10}$ wherein
  R$^7$ represents hydrogen, methyl or C2–C4 alkyl, where the C2–C4 alkyl are unsubstituted or substituted by NR$^5$R$^6$, wherein R$^5$ and R$^6$ have the previously defined meanings;
  R$^8$, R$^9$ which may be the same or different, represent hydrogen, methyl or C2–C4 alkyl, where the C2–C4 alkyl are unsubstituted or substituted by NR$^5$R$^6$ wherein R$^5$ and R$^6$ have the previously defined meanings;
  R$^{10}$ represents hydrogen, methyl or C2–C4 alkyl, where the C2–C4 alkyl are unsubstituted or substituted by one or more NR$^5$R$^6$ or NHC(=NH)NH$_2$, wherein R$^5$ and R$^6$ have the previously defined meanings;

the symbol ⁓ means Z or E configuration;
R$^7$, R$^8$, R$^9$ taken two may form, together with the heteroatoms they are linked to, and where possible, a five- or six- or seven-membered heterocyclic ring.

Where the compounds of formula (I) can exhibit tautomerism, the formula is intended to cover all tautomers; the invention encompasses within its scope all the possible stereoisomers, Z and E isomers, where formula (I) permits, and their mixtures, optical isomers and their mixtures, the metabolites and the metabolic precursors of compound of formula (I).

Also the pharmaceutical acceptable salts are included in the scope of the invention. Pharmaceutical acceptable salts are salts which retain the biological activity of the base and are derived from such known pharmacologically acceptable acids such as, e.g., hydrochloric, hydrobromic, sulfuric, phosphoric, fumaric, succinic, oxalic, malic, tartaric, maleic, citric, methanesulfonic or benzoic acid and others commonly used in the art.

The compounds of the invention also include solvates (e.g. hydrates).

N-oxides, where the nitrogen atom is not substituted with a hydrogen atom, are also encompassed by the invention.

The alkyl groups are branched or straight chain groups or cyclic groups.

The C2–C4 alkyl is preferably ethyl, n-propyl, iso-propyl, n-butyl or tert-butyl.

The R$^1$ group is preferably hydrogen, 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl.

The R$^7$ group is preferably hydrogen, methyl, 2-aminoethyl, 3-aminopropyl, 2-dimethylaminoethyl, 3-dimethylaminopropyl, 2-(1-pyrrolidinyl)ethyl, 3-(1-pyrrolidinyl)propyl.

The NR$^8$R$^9$ group is preferably amino, methylamino, dimethylamino, diethylamino, iso-propylamino, pyrrolidinyl, piperidyl, morfolino, piperazin-1-yl, 4-methylpiperazin-1-yl, 4-(2-dimethylaminoethyl) piperazin- 1-yl, 2-dimethylaminoethylamino, 2-diethylaminoethylamino, (2-dimethylaminoethyl) methylamino, (2-diethylaminoethyl)methylamino, 3-dimethylaminopropylamino, (3-dimethylaminopropyl) methylamino, 2-(1-pyrrolidinyl)ethylamino, 3-(1-pyrrolidinyl)propylamino, (2-(1-pyrrolidinyl)ethyl) methylamino.

The R$^{10}$ group is preferably 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl, 2-guanidinoethyl, 3-guanidinopropyl.

R$^7$ and R$^8$ groups taken together with the heteroatom they are linked to, are preferably 2-imidazolin-2-yl, 1-methyl-2-imidazolin-2-yl, 2-imidazolyl, 2-(1-methyl)imidazolyl, 1,4,5,6-tetrahydro-2-pyrimidinyl, 1-methyl-1,4,5,6-tetrahydro-2-pyrimidinyl.

Preferred examples of specific compounds according to the present invention are (E,E)-17β-(3-guanidinoimino-2-methyl-1-propenyl)-5β-androstane-3β,14β-diol (E,E)-17β-[3-(2-imidazolin-2-yl)hydrazono-2-methyl-1-propenyl]-5β-androstane-3β,14β-diol (E,E)-17β-[3-(1-methyl-2-imidazolin-2-yl)hydrazono-2-methyl-1-propenyl]-5β-androstane-3β,14β-diol (E,E)-17β-[3-(2-imidazolyl)hydrazono-2-methyl-1-propenyl]-5β-androstane-3β,14β-diol (E,E)-17β-[3-(1,4,5,6-tetrahydro-2-pyrimidinyl)
hydrazono-2-methyl-1-propenyl]-5β-androstane-3β,
14β-diol (E,E)-17β-[3-[3-(2-dimethylaminoethyl)guanidinoimino]
-2-methyl-1-propenyl]-5β-androstane-3β,14β-diol (E,E)-17β-[3-(2-aminoethoxyimino)-2-methyl-1-
propenyl]-5β-androstane-3β,14β-diol (E,E)-17β-[3-(3-aminopropoxyimino)-2-methyl-1-
propenyl]-5β-androstane-3β,14β-diol (E,E)-17β-[3-(2-dimethylaminoethoxyimino)-2-methyl-
1-propenyl]-5β-androstane-3β,14β-diol (E,E)-17β-[3-(3-dimethylaminopropoxyimino)-2-
methyl-1-propenyl]-5β-androstane-3β,14β-diol (E,E)-17β-[3-(2-guanidinoethoxyimino)-2-methyl-1-
propenyl]-5β-androstane-3β,14β-diol (E,E)-17β-[3-(3-guandinopropoxyimino)-2-methyl-1-
propenyl]-5β-androstane-3β,14β-diol (E,E)-17β-(3-guanidinoimino-2-ethyl-1-propenyl)-5β-
androstane-3β,14β-diol (E,E)-17β-[3-(2-imidazolin-2-
yl)hydrazono-2-ethyl-1-propenyl]-5β-androstane-3β,
14β-diol (E,E)-17β-[3-(1,4,5,6-tetrahydro-2-pyrimidinyl)
hydrazono-2-ethyl-1-propenyl]-5β-androstane-3β,14β-
diol (E,E)-17β-[3-(2-aminooethoxyimino)-2-ethyl-1-
propenyl]-5β-androstane-3β,14β-diol (E,E)-17β-[3-(3-aminopropoxyimino)-2-ethyl-1-
propenyl]-5β-androstane-3β,14β-diol (E,E)-17β-[3-(2-dimethylaminoethoxyimino)-2-ethyl-1-
propenyl]-5β-androstane-3β,14β-diol (E,E)-17β-[3-(3-dimethylaminopropoxyimino)-2-ethyl-
1-propenyl]-5β-androstane-3β,14β-diol (E,E)-17β-[3-(2-guanidinoethoxyimino)-2-ethyl-1-
propenyl]-5β-androstane-3β,14β-diol (E,E)-17β-[3-(3-guanidinopropoxyimino)-2-ethyl-1-
propenyl]-5β-androstane-3β,14β-diol and the corresponding 3β-(2-aminoethyl), 3β-(2-dimethylaminoethyl), 3β-(2-(1-pyrrolidinyl)ethyl), 3β-(3-aminopropyl), 3β-(3-dimethylaminopropyl) and 3β-(3-(1-pyrrolidinyl)propyl) ethers of the compounds mentioned above;

and the corresponding 3α-hydroxy compounds of the 3β-hydroxy derivatives;

and the corresponding 3α-(2-aminoethyl), 3α-(2-dimethylaminoethyl), 3α-(2-(1-pyrrolidinyl)ethyl) 3α-(3-aminopropyl), 3α-(3-dimethylaminopropyl) and 3α-(3-(1-pyrrolidinyl)propyl) ethers of the compounds mentioned above;

and the corresponding 17α-hydroxy compounds of the compounds mentioned above.

The invention furthermore provides a process for the preparation of compounds of general formula (I), which comprises a condensation reaction of compounds of formula (II)

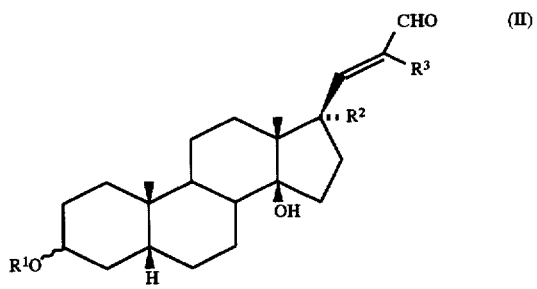

in which $R^1$, $R^2$, $R^3$ and the symbol ⁓ are as above defined, with a compound of general formula (III) and (IV)

to give compounds of general formula (I). Compounds (III) and (IV) can be used as the free base or in the form of a salt with an acid such as, e.g., hydrochloric, hydrobromic, hydriodic, carbonic, oxalic or sulfuric acid. The reaction can be carried out in a solvent, such as ethanol, methanol, acetonitrile, dioxane, tetrahydrofuran, water or a mixture of said solvents, at a temperature between 0° C. and the boiling point of the solvents mentioned above or of their mixtures. To the reaction mixtures, additional salts, such as, e.g., $NaH_2PO_4$, $Na_2HPO_4$, NaOAc, can be added as well as acids such as, e.g., hydrochloric, hydrobromic, sulfuric, acetic, phosphoric acid, and bases such as, e.g., sodium or potassium hydroxide, to maintain the desired pH.

The groups optionally present in $R^1$ and/or $R^2$ are protected, if necessary, by known methods, to give after removal by known methods of protective groups, if any, compounds of general formula (I) which can be converted into other compounds of general formula (I) by known methods.

Compounds of general formula (I) where $R^1$, $R^2$, $R^3$, and the symbol ⁓ are as above defined and $R^4$ represents $OR^{10}$ wherein $R^{10}$ contains a guanidino group can be obtained from other compounds of general formula (I) where $R^1$, $R^2$, $R^3$, and the symbol ⁓ are as above defined and $R^4$ represents $OR^{10}$ wherein $R^{10}$ contains a primary amino group e.g. by reaction with 1-amidino-3,5-dimethylpyrazole nitrate or S-methylisothiourea.

Compounds of general formula (II) are prepared with methods well known to those skilled in the art.

For example compounds of general formula (II) in which $R^1$ and $R^2$ are hydrogen, $R^3$ and the symbol ⁓ are as above defined, are prepared from the known 3β,14β-dihydroxy-5β-androstane-17β-carboxaldehyde (Boutagy J. and Thomas R., Aust. J. Chem., 1971, 24, 2723) or from the unknown 3α,14β-dihydroxy-5β-androstane-17β-carboxaldehyde by reaction with trimethyl 2-phosphonopropionate, triethyl 2-phosphonopropionate, trimethyl 2-phosphonobutirrate or triethyl 2-phosphonobutirrate in the presence of a base, for example sodium hydride or di-iso-propylethylamine in the presence of lithium chloride, followed by reduction of the ester function to the corresponding alcohol, for example with di-iso-butylaluminum hydride, and subsequent allylic oxidation to the unsaturated aldehyde, for example with manganese dioxide.

For example compounds of general formula (II) in which $R^1$ is hydrogen, $R^2$ is hydroxy, $R^3$ and the symbol ⁓ are as above defined, are prepared from the known ethyl (E)-3β, 14β-dihydroxy-21-methyl-5β-pregn-20-ene-21-carboxylate (Boutagy J. and Thomas R., *Aust. J. Pharm Sci.*, 1972, NS1, 67) or from the unknown ethyl (E)-3β,14β-dihydroxy-21-ethyl-5β-pregn-20-ene-21-carboxylate, ethyl (E)-3α,14β-dihydroxy-21-methyl-5β-pregn-20-ene-21-carboxylate or ethyl (E)-3α,14β-dihydroxy-21-ethyl-5β-pregn-20-ene-21-carboxylate by allylic oxidation, for example with selenium dioxide, followed by reduction of the ester function to the corresponding alcohol, for example with di-isobutylaluminum hydride, and subsequent allylic oxidation to the unsaturated aldehyde, for example with manganese dioxide.

For example the unknown 3α-hydroxy compounds are prepared from the corresponding known 3-keto compounds by reduction with sodium borohydride, lithium aluminumhydride or lithium aluminum-tri-tert-butoxyhydride. The corresponding unknown 3-keto compounds are obtained from the 3β-hydroxy derivative by oxidation with known methods such as Jones reagent, chromic anhydride in pyridine or tetrapropylammonium perruthenate and N-methylmorpholine N-oxide.

Compounds (II) in which $R^2$, $R^3$ and the symbol  are as above defined and where $R^1$ is different from hydrogen, are prepared from the corresponding compounds (II) where $R^1$ is hydrogen by reaction with a compound of formula (V)

$$R^{11}W \qquad (V)$$

where $R^{11}$ is as defined for $R^1$, but different from hydrogen, or a group convertible to $R^1$ and W is an electron-withdrawing group, such as halogen, mesyloxy, or tosyloxy group, which confers electrophilic properties to the attached carbon atom, and $R^1$ is as above defined. The reaction is best carried out in an inert aprotic solvent, such as tetrahydrofuran, dioxane, dimethylformamide, dimethylsulfoxyde or in neat $R^{11}W$ and in the presence of a base, e.g. sodium or potassium hydride, at a temperature ranging from 0° C. to 110° C.

In all the transformations mentioned above the hydroxy group optionally present in $R^2$ and the aldehydic function are protected, if necessary, by known methods to give, after removal by known methods of protective groups, if any, a compound of general formula (II).

Said transformations are only examples of well established procedures described in Organic Chemistry (see for example: J. March "Advanced Organic Chemistry". J. Wiley & Sons, 1985: D. Barton and W. D. Ollis "Comprehensive Organic Chemistry", Pergamon Press, 1979) well known to those skilled in the art.

Compounds of general formula (III), (IV) and (V) are known compounds, generally commercially available or preparable from known compounds by known methods.

The following examples illustrate the invention without limiting it.

EXAMPLE 1

(E,E)-17β-(3-Guanidinoimino-2-methyl-1-propenyl)-5β-androstane-3β,14β-diol (I-aa)

A mixture of 0.50 g of aminoguanidine hydrogencarbonate in 10 ml of water and 30 ml of dioxane was made acid to pH 3 with 3N HCl. A solution of 0.95 g of (E)-3β,14β-dihydroxy-21-methyl-5β-pregn-20-ene-21-carboxaldehyde (Prepn. 1) in 10 ml of dioxane was added at room temperature. After 3 days the mixture was evaporated to dryness under reduced pressure. The crude product was purified by flash chromatography (SiO₂) using chloroform/methanol/28% ammonium hydroxide 80/20/3 as the eluant: the fractions containing the title compound were collected and evaporated to dryness. The residue was ground with diethyl ether and ethanol to give 0.75 g of the title compound (I-aa) as a white solid.

¹H-NMR (300 MHz, CD3OD, ppm from TMS): 0.86 (3H, s); 0.98 (3H, s); 1.68 (3H, d); 2.65–2.75 (1H, m); 4.05 (1H, s); 5.90 (1H, dq); 7.62 (1H, s).

EXAMPLE 2

(E,E)-17β-[3-(2-Imidazolin-2-yl)hydrazono-2-methyl-1-propenyl]-5β-androstane-3β,14β-diol (I-ab)

A solution of 0.55 g of 2-hydrazino-2-imidazoline hydrobromide in 10 ml of water and 30 ml of dioxane was made acid to pH 3 with 0.1N HBr. A solution of 1.00 g of (E)-3β,14β-dihydroxy-21-methyl-5β-pregn-20-ene-21-carboxaldehyde (Prepn. 1) in 10 ml of dioxane was added at room temperature. After 3 days, the solution was evaporated to dryness under reduced pressure. The crude product was purified by flash chromatography (SiO₂) using chloroform/methanol/28% ammonium hydroxide 90/10/1 as the eluant: the fractions containing the title compound were collected and evaporated to dryness. The residue was ground with ethyl acetate and ethanol to give 0.85 g of the title compound (I-ab) as a white solid.

¹H-NMR (300 MHz, CD₃OD, ppm from TMS): 0.86 (3H, s); 0.98 (3H, s); 1.68 (3H, d); 2.65–2.75 (1H, m); 3.50 (4H, s); 4.05 (1H, s); 5.92 (1H, dq); 7.61 (1H, s).

EXAMPLE 3

(E,E)-17β-[3-(1-Methyl-2-imidazolin-2-yl)hydrazono-2-methyl-1-propenyl]-5β-androstane-3β,14β-diol (I-ac)

The title compound (I-ac) (0.52 g) was obtained as a white solid, starting from (E)-3β,14β-dihydroxy-21-methyl-5β-pregn-20-ene-21-carboxaldehyde (0.84 g) (Prepn. 1) and 1-methyl-2-hydrazino-2-imidazoline hydroiodide (prepared from 2-methylthio-1-methyl-2-imidazoline hydroiodide and hydrazine following the procedure described in Houben-Weil, Metoden der Organischen Chemie, Band VIII, page 183) using the same procedure described in Ex. 1.

¹H-NMR (300 MHz, CD₃OD, ppm from TMS): 0.87 (3H, s); 0.99 (3H, s); 1.68 (3H, d); 2.65–2.75 (1H, m); 3.00 (3H, s); 3.50 (4H, s); 4.05 (1H, s); 5.90 (1H, dq); 7.60 (1H, q).

EXAMPLE 4

(E,E)-17β-[3-(1,4,5,6-Tetrahydro-2-pyrimidinyl)hydrazono-2-methyl-1-propenyl]-5β-androstane-3β,14β-diol (I-ad)

The title compound (I-ad) (0.65 g) was obtained as a white solid, starting from (E)-3β,14β-dihydroxy-21-methyl-5β-pregn-20-ene-21-carboxaldehyde (0.90 g) (Prepn. 1) and 2-hydrazino-1,4,5,6-tetrahydro-2-pyrimidine hydroiodide (prepared from 2-methylthio-1,4,5,6-tetrahydro-2-pyrimidine hydroiodide and hydrazine following the procedure described in Houben-Weil, Metoden der Organischen Chemie, Band VIII, page 183) using the same procedure described in Ex. 1.

¹H-NMR (300 MHz, CD₃OD, ppm from TMS): 0.86 (3H, s); 0.98 (3H, s); 1.68 (3H, d); 2.65–2.75 (1H, m); 3.15 (4H, m); 4.05 (1H, s); 5.90 (1H, dd); 7.60 (1H, s).

EXAMPLE 5

(E,E)-17β-{3-[3-(2-Dimethylaminoethyl)guanidinoimino]-2-methyl-1-propenyl}-5β-androstane-3β,14β-diol (I-ae)

The title compound (I-ae) (0.50 g) was obtained as a white solid, starting from (E)-3β,14β-dihydroxy-21-methyl-5β- pregn-20-ene-21-carboxaldehyde (0.78 g) (Prepn. 1) and 1-amino-3-(2-dimethylaminoethyl)guanidine hydroiodide (prepared following the procedure described in Houben-Weil, Metoden der Organischen Chorale, Band VIII, page 183) using the same procedure described in Ex. 1.

$^1$H-NMR (300 MHz, CD$_3$OD, ppm from TMS): 0.87 (3H, s); 0.98 (3H, s); 1.67 (3H, d); 2.65–2.75 (1H, m); 2.40 (6H, s); 2.70 (2H, t); 3.50 (2H, t); 4.05 (1H, s); 6.90 (1H, dq); 7.60 (1H, s).

EXAMPLE 6

(E,E)-17β-[3-(2-Aminoethoxyimino)-2-methyl-1-propenyl]-5β-androstone-3β,14β-diol (I-af)

A solution of 0.36 g of 2-aminoethoxyamine dihydrochloride and 0.82 g of sodium acetate in 20 ml of water and 40 ml of dioxane was brought to pH 4.5 by adding 3N HCl. A solution of 0.72 g of (E)-3β,14β-dihydroxy-21-methyl-5β-pregn-20-ene-21-carboxaldehyde (Prepn. 1) in 16 ml of dioxane and 8 ml of water was added dropwise at room temperature. After 4 hrs the solution was concentrated under reduced pressure and the mixture brought to pH 9.0 with 10% Na$_2$CO$_3$ and extracted with methylene chloride. The organic phase was dried over anhydrous Na$_2$SO$_4$ and evaporated to dryness under reduced pressure. The residue was purified by flash chromatography (SiO$_2$) using chloroform/methanol/28% ammonium hydroxide 90/10/1 as the eluant. The fractions containing the title compound were collected and evaporated to dryness. The residue was dissolved in ethyl acetate and to the solution was added the stoichiometric amount of an ethanolic solution of fumaric acid. The crystals were collected to give 0.82 g of the title compound (I-af) as a fumarate, white solid.

$^1$H-NMR (300 MHz, CD3OD, ppm from TMS): 0.86 (3H, s); 0.98 (3H, s); 1.68 (3H, d); 2.65–2.75 (1H, m); 3.22 (2H, m); 4.05 (1H, m); 4.22 (2H, m); 6.04 (1H, dq); 6.70 (2H, s); 7.78 (1H, s).

EXAMPLE 7

(E,E)-17β-[3-(3-Aminopropoxyimino)-2-methyl-1-propenyl-5β-androstane-3β,14β-diol (I-ag)

The title compound (I-ag) (0.45 g) was obtained as a fumarate, white solid, starting from (E)-3β,14β-dihydroxy-21-methyl-5β-pregn-20-ene-21-carboxaldehyde (0.42 g) (Prepn. 1) and 3-aminopropoxyamine dihydrochloride using the same procedure described in Ex. 6.

$^1$H-NMR (300 MHz, CD$_3$OD, ppm from TMS): 0.86 (3H, s); 0.98 (3H, s); 1.68 (3H, d); 2.65–2.75 (1H, m); 3.15 (2H, m); 4.05 (1H, m); 4.15 (2H, m); 6.04 (1H, dq); 6.70 (2H, s); 7.78 (1H, s).

EXAMPLE 8

(E,E)-17β-[3-(2-Dimethylaminoethoxyimino)-2-methyl-1-propenyl]-5β-androstane-3β,14β-diol (I-ah)

The title compound (I-ah) (0.64 g) was obtained as a fumarate, white solid, starting from (E)-3β,14β-dihydroxy-21-methyl-5β-pregn-20-ene-21-carboxaldehyde (0.60 g) (Prepn. 1) and 2-dimethylaminoethoxyamine dihydrochloride using the same procedure described in Ex. 6.

$^1$H-NMR (300 MHz, CD$_3$OD, ppm from TMS): 0.86 (3H, s); 0.98 (3H, s); 1.68 (3H, d); 2.65–2.75 (1H, m); 2.90 (6H, s); 3.42 (2H, m); 4.05 (1H, m); 4.35 (2H, m); 6.06 (1H, dq); 6.70 (2H, s); 7.78 (1H, s).

EXAMPLE 9

(E,E)-17β-[3-(3-Dimethylaminopropoxyimino)-2-methyl-1-propenyl]-5β-androstane-3β,14β-diol (I-ai)

The title compound (I-ai) (0.42 g) was obtained as a fumarate, white solid, starting from (E)-3β,14β-dihydroxy-5β-pregn-20-ene-21-carboxaldehyde (0.39 g) (Prepn. 1) and 3-dimethylaminopropoxyamine dihydrochloride using the same procedure described in Ex. 6.

$^1$H-NMR (300 MHz, CD$_3$OD, ppm from TMS): 0.86 (3H, s); 0.98 (3H, s); 1.68 (3H, d); 2.65–2.75 (1H, m); 2.85 (6H, s); 3.30 (2H, m); 4.05 (1H, m); 4.25 (2H, t); 6.06 (1H, dq); 6.70 (2H, s); 7.78 (1H, s).

EXAMPLE 10

(E,E)-17β-[3-(2-Guanidinoethoxyimino)-2-methyl-1-propenyl]-5β-androstane-3β,14β-diol (I-ai)

A solution of 0.50 g of (E,E)-17β-[3-(2-aminooethoxyimino)-21-methyl-1-propenyl]5β-androstane-3β,14β-diol (I-af) and 0.55 g of 1-amidino-3,5-dimethylpyrazole nitrate in 10 ml of ethanol was heated at reflux for 10 hrs. The solution was evaporated to dryness under reduced pressure and the crude product was ground with water and then with diethyl ether/ethanol to give 0.35 g of the title compound (I-aj) as a nitrate, white solid.

$^1$H-NMR (300 MHz, CD$_3$OD, ppm from TMS): 0.86 (3H, s); 0.97 (3H, s); 1.68 (3H, d); 2.65–2.75 (1H, m); 3.40 (2H, m); 4.05 (1H, s); 4.30 (2H, m); 6.05 (1H, dq); 7.77 (1H, s).

EXAMPLE 11

(E,E)-17β-[3-(3-Guanidinopropoxyimino)-2-methyl-1-propenyl]-5β-androstane-3β,14β-diol (I-ak)

The title compound (I-a) (0.31 g) was obtained as a nitrate salt, white solid, starting from (E,E)-17β-[3-(3-aminopropoxyimino)-21-methyl-1-propenyl]-5(β-androstane-3β,14β-diol (I-ag) (0.45 g) and 1-amidino-3,5-dimethylpyrazole nitrate using the procedure described in Ex. 10.

$^1$H-NMR (300 MHz, CD$_3$OD, ppm from TMS): 0.86 (3H, s); 0.97 (3H, s); 1.68 (3H, d); 2.65–2.75 (1H, m); 3.35 (2H, m); 4.05 (1H, m); 4.25 (2H, t); 6.05 (1H, dq); 7.78 (1H, s).

EXAMPLE 12

(E,E)-17β-(3-Guanidinoimino-2-ethyl-1-propenyl)-5β-androstane-3β,14β-diol (I-al)

The title compound (I-al) (0.32 g) was obtained as a white solid, starting from (E)-3β,14β-dihydroxy-21-ethyl-5β-pregn-20-ene-21-carboxaldehyde (0.35 g) (Prepn. 2) and aminoguanidine hydrogencarbonate using the same procedure described in Ex. 1.

$^1$H-NMR (300 MHz, CD$_3$OD, ppm from TMS): 0.86 (3H, s); 0.98 (3H, s); 2.65–2.75 (1H, m); 4.05 (1H, s); 5.90 (1H, dq); 7.62 (1H, s).

EXAMPLE 13

(E,E)-17β-[3-(2-Aminoethoxyimino)-2-ethyl-1-propenyl]-5β-androstane-3β,14β-diol (I-am)

The title compound (I-am) (0.33 g) was obtained as a fumarate, white solid, starting from (E)-3β,14β-dihydroxy-21-ethyl-5β-pregn-20-ene-21-carboxaldehyde (0.42 g) (Prepn. 2) and 2-aminoethoxyamine dihydrochloride using the same procedure described in Ex. 6.

$^1$H-NMR (300 MHz, CD$_3$OD, ppm from TMS): 0.86 (3H, s); 0.98 (3H, s); 2.65–2.75 (1H, m); 3.22 (2H, m); 4.05 (1H, m); 4.22 (2H, m); 6.05 (1H, dq); 6.70 (2H, s); 7.78 (1H, s).

EXAMPLE 14

(E,E)-17β-[3-(3-Aminopropoxyimino)-2-ethyl-1-propenyl]-5β-androstane-3β,14β-diol (I-an)

The title compound (I-an) (0.29 g) was obtained as a fumarate, white solid, starting from (E)-3β,14β-dihydroxy-21-ethyl-5β-pregn-20-ene-21-carboxaldehyde (0.27 g) (Prepn. 2) and 3-aminopropoxyamine dihydrochloride using the same procedure described in Ex. 6.

¹H-NMR (300 MHz, CD₃OD, ppm from TMS): 0.86 (3H, s); 0.98 (3H, s); 2.65–2.75 (1H, m); 3.15 (2H, m); 4.05 (1H, m); 4.15 (2H, m); 6.04 (1H, dq); 6.70 (2H, s); 7.78 (1H, s).

EXAMPLE 15

(E,E)-17β-[3-(2-Dimethylaminoethoxyimino)-2-ethyl-1-propenyl]-5β-androstane-3β,14β-diol (I-ao)

The title compound (I-ao) (0.34 g) was obtained as a fumarate, white solid, starting from (E)-3β,14β-dihydroxy-21-ethyl-5β-pregn-20-ene-21-carboxaldehyde (0.30 g) (Prepn. 2) and 2-dimethylaminoethoxyamine dihydrochloride using the same procedure described in Ex. 6.

¹H-NMR (300 MHz, CD₃OD, ppm from TMS): 0.86 (3H, s); 0.98 (3H, s); 2.65–2.75 (1H, m); 2.90 (6H, s); 3.40 (2H, m); 4.05 (1H, m); 4.35 (2H, m); 6.05 (1H, dq); 6.70 (2H, s); 7.78 (1H, s).

EXAMPLE 16

(E,E)-17β-[3-(3-Dimethylaminopropoxyimino)-2-ethyl-1-propenyl]-5β-androstane-3β,14β-diol (I-ap)

The title compound (I-ap) (0.31 g) was obtained as a fumarate, white solid, starting from (E)-3β,14β-dihydroxy-21-ethyl-5β-pregn-20-ene-21-carboxaldehyde (0.30 g) (Prepn. 2) and 3-dimethylaminopropoxyamine dihydrochloride using the same procedure described in Ex. 6.

¹H-NMR (300 MHz, CD₃OD, ppm from TMS): 0.86 (3H, s); 0.98 (3H, s); 2.65–2.75 (1H, m); 2.85 (6H, s); 3.30 (2H, m); 4.05 (1H, m); 4.25 (2H, t); 6.05 (1H, dq); 6.70 (2H, s); 7.78 (1H, s).

EXAMPLE 17

(E,E)-17β-(3-Guanidinoimino-2-methyl-1-propenyl]-5β-androstane-3β,14β,17α-triol (I-aq)

The title compound (I-aq) (0.23 g) was obtained as a white solid, starting from (E)-3β,14β,17α-trihydroxy-21-methyl-5β-pregn-20-ene-21-carboxaldehyde (Prepn. 3) (0.30 g) and aminoguanidine hydrogencarbonate using the procedure described in Ex. 1.

¹H-NMR (300 MHz, CD₃OD, ppm from TMS): 0.85 (3H, s); 0.96 (3H, s); 1.67 (3H, d); 4.05 (1H, s); 5.90 (1H, m); 7.63 (1H, s).

EXAMPLE 18

(E,E)-17β-[3-(2-Aminoethoxyimino)-2-methyl-1-propenyl]-5β-androstane-3β,14β,17α-triol (I-ar)

The title compound (I-ar) (0.33 g) was obtained as a fumarate, white solid, starting from (E)-3β,14β,17α-trihydroxy-21-methyl-5β-pregn-20-ene-21-carboxaldehyde (0.42 g) (Prepn. 3) and 2-aminoethoxyamine dihydrochloride using the same procedure described in Ex. 6.

¹H-NMR (300 MHz, CD₃OD, ppm from TMS): 0.86 (3H, s); 0.97 (3H, s); 1.68 (3H, d); 3.20 (2H, m); 4.05 (1H, m); 4.20 (2H, m); 6.05 (1H, dq); 6.70 (2H, s); 7.78 (1H, s).

EXAMPLE 19

(E,E)-17β-[3-(2-Dimethylaminoethoxyimino)-2-methyl-1-propenyl]-5β-androstane-3β,14β,17α-triol (I-as)

The title compound (I-as) (0.32 g) was obtained as a fumarate, white solid, starting from (E)-3β,14β,17α-trihydroxy-21-methyl-5β-pregn-20-ene-21-carboxaldehyde (Prepn. 3) (0.30 g) and 2-dimethylaminoethoxyamine dihydrochloride using the same procedure described in Ex. 6.

¹H-NMR (300 MHz, CD₃OD, ppm from TMS): 0.86 (3H, s); 0.98 (3H, s); 1.68 (3H, d); 2.90 (6H, s); 3.40 (2H, m); 4.05 (1H, m); 4.35 (2H, m); 6.05 (1H, dq); 6.70 (2H, s); 7.77 (1H, s).

EXAMPLE 20

(E,E)-3 6-[2-(1-Pyrrolidinyl)ethoxy]-17β-(3-guanidinoimino-2-methyl-1-propenyl]-5β-androstane-14β-ol (I-at)

A solution of 0.50 g (E)-3β-[2-(1-pyrrolidinyl)ethoxy]-21-[2-(1,3-dioxolanyl)]-21-methyl-5β-pregn-20-ene-14β-ol (Prepn. 4) and 15 ml of 0.1M hydrochloric acid in 40 ml of dioxane was kept at room temperature. After 1 day, 0.15 g of aminoguanidine hydrogencarbonate were added. After 3 days the solution was evaporated to dryness under reduced pressure. The crude product was purified by flash-chromatography (SiO₂) using chloroform/methanol/28% ammonium hydroxide 80/20/3 as the eluant; the fractions containing the title compound were collected and evaporated to dryness. The residue was triturated with diethyl ether/ethanol to give 0.30 g of the title compound (I-at) as a white solid.

¹H-NMR (300 MHz, CD₃OD, ppm from TMS): 0.86 (3H, s); 0.98 (3H, s); 1.68 (3H, d); 2.65–2.75 (1H, m); 2.80–2.95 (6H, m); 3.65 (3H, m); 5.90 (1H, dq); 7.62 (1H, s).

EXAMPLE 21

(E,E)-3β-[2-(1-Pyrrolidinyl)ethoxyl-17β-[3-(2-aminoethoxyimino)-2-methyl-1-propenyl]-5β-androstane-14β-ol (I-au)

The title compound (I-au) (0.34 g) was obtained as a white solid, starting from (E)-3β-[2-(1-pyrrolidinyl)ethoxy]-21-[2-(1,3-dioxolanyl)]-21-methyl-5β-pregn-20-ene-14β-ol (Prepn. 4) (0.43 g) and 2-aminoethoxyamine dihydrochloride using the same procedure described in Ex. 20.

¹H-NMR (300 MHz, CD₃OD, ppm from TMS): 0.86 (3H, s); 0.97 (3H, s); 1.68 (3H, d); 2.65–2.75 (1H, m); 2.80–3.00 (8H, m); 3.60–3.75 (3H, m); 4.05 (2H, t); 5.98 (1H, m); 7.70 (1H, s).

EXAMPLE 22

(E,E)-3β-[2-(1-Pyrrolidinyl)propoxy]-17β-[3-guanidinoimino-2-methyl-1-propenyl]-5β-androstane-4β-ol (I-av)

The title compound (I-av) (0.27 g) was obtained as a white solid, oxalate, starting from (E)-3β-[2-(1-pyrrolidinyl)propoxy]-21-[2-(1,3-dioxolanyl)]-21-methyl-5β-pregn-20-ene-14β-ol (Prepn. 5) (0.34 g) and aminoguanidine hydrogencarbonate using the same procedure described in Ex. 20.

¹H-NMR (300 MHz, CD₃OD, ppm from TMS): 0.86 (3H, s); 0.98 (3H, s); 1.68 (3H, d); 2.60–2.80 (7H, m); 3.45–3.70 (3H, m); 5.90 (1H, dq); 7.60 (1H, s).

EXAMPLE 23

(E,E)-3β-[2-(1-Pyrrolidinyl)propoxy]-17β-[3-(2-aminoethoxyimino)-2-methyl-1-propenyl]-5β-androstane-14β-ol (I-aw)

The title compound (I-aw) (0.23 g) was obtained as a white solid, starting from (E)-3β-[2-(1-pyrrolidinyl)propoxy]-21-[2-(1,3-dioxolanyl)]-21-methyl-5β-pregn-20-ene-14β-ol (Prepn. 5) (0.35 g) and 2-aminoethoxyamine dihydrochloride using the same procedure described in Ex. 20, followed by salification with the stoichiometric amount of oxalic acid.

$^1$H-NMR (300 MHz, CD$_3$OD, ppm from TMS): (3H, s); 0.97 (3H, s); 1.68 (3H, d); 2.60–2.80 (7H, m); 2.90 (2H, t); 3.45–3.70 (3H, m); 4.06 (2H, t); 5.97 (1H, m); 7.70 (1H, s).

EXAMPLE 24

(E,E)-(3β-(2-Aminoethoxyl-17β-(3-guanidinoimino-2-methyl-1-propenyl)-5β-androstane-4β-ol (I-ax)

The title compound (I-ax) (0.24 g) was obtained as a white solid, starting from (E)-3β-(3-aminoethoxy)-21-[2-(1,3-dioxolanyl)]-21-methyl-5β-pregn-20-ene-14β-ol (Prepn. 6) (0.40 g) and aminoguanidine hydrogencarbonate using the same procedure described in Ex. 20.

$^1$H-NMR (300 MHz, CD$_3$OD, ppm from TMS): 0.86 (3H, s); 0.98 (3H, s); 1.68 (3H, d); 2.65–2.75 (1H, m); 3.00 (2H, m); 3.40 (2H, m); 3.70 (1H, s); 5.90 (1H, dq); 7.62 (1H, s).

EXAMPLE 25

(E,E)-3β-(2-Aminoethoxy)-17β-[3-(2-aminoethoxyimino)-2-methyl-1-propenyl]-5β-androstane-14β-ol (I-av)

The title compound (I-ay) (0.25 g) was obtained as a white solid, starting from (E)-3β-(2-aminoethoxy)-21-(2-(1,3-dioxolanyl)]-21-methyl-5β-pregn-20-ene-14β-ol (Prepn. 6) (0.36 g) and 2-aminoethoxyamine dihydrochloride using the same procedure described in Ex. 20.

$^1$H-NMR (300 MHz, CD$_3$OD, ppm from TMS): 0.86 (3H, s); 0.97 (3H, s); 1.68 (3H, d); 2.65–2.75 (1H, m); 2.90–3.00 (4H, m); 3.40 (2H, t); 3.65 (1H, m); 4.05 (2H, t); 5.98 (1H, m); 7.70 (1H, s).

EXAMPLE 26

(E,E)-3β-(3-Aminopropoxy)-17β-(3-guanidinoimino-2-methyl-1-propenyl)-5β-androstane-4β-ol (I-az)

The title compound (I-az) (0.26 g) was obtained as a white solid, starting from (E)-3β-(3-aminopropoxy)-21-[2-(1,3-dioxolanyl)]-21-methyl-5β-pregn-20-ene-14β-ol (Prepn. 7) (0.34 g) and aminoguanidine hydrogencarbonate using the same procedure described in Ex. 20.

$^1$H-NMR (300 MHz, CD$_3$OD, ppm from TMS): 0.86 (3H, s); 0.98 (3H, s); 1.67 (3H, d); 2.60–2.80 (3H, m); 3.30–3.40 (2H, m); 3.60 (1H, m); 5.90 (1H, dq); 7.60 (1H, s).

EXAMPLE 27

(E,E)-3β-(3-Aminopropoxy)-17β-[3-(2-aminoethoxyiminol-2-methyl-1-propenyl]-5β-androstane-14β-ol (I-ba)

The title compound (I-ba) (0.23 g) was obtained as a white solid, starting from (E)-3β-(3-aminopropoxy)-21-[2-(1,3-dioxolanyl)]-21-methyl-5β-pregn-20-ene-14β-ol (Prepn. 7) (0.35 g) and 2-aminoethoxyamine dihydrochloride using the same procedure described in Ex. 20.

$^1$H-NMR (300 MHz, CD$_3$OD, ppm from TMS): 0.86 (3H, s); 0.97 (3H, s); 1.68 (3H, d); 2.60–2.80 (3H, m); 2.90 (2H, t); 3.30–3.40 (2H, m); 3.60 (1H, m); 4.05 (2H, t); 5.98 (1H, m); 7.70 (1H, s).

EXAMPLE 28

(E,E)-17β-(3-Guanidinoimino-2-methyl-1-propenyl)-5β-androstane-3α,14β-diol (I-bb)

The title compound (I-bb) (0.28 g) was obtained as a white solid starting from (E)-3α,14β-dihydroxy-21-methyl-5β-pregn-20-ene-21-carboxaldehyde (Prepn. 8) (0.40 g) and aminoguanidine hydrogencarbonate using the same procedure described in Ex. 1.

$^1$H-NMR (300 MHz, CD$_3$OD, ppm from TMS): 0.86 (3H, s); 0.98 (3H, s); 1.68 (3H, d); 2.65–2.75 (1H, m); 3.75 (1H, s); 5.90 (1H, dq); 7.62 (1H, s).

EXAMPLE 29

(E,E)-17β-[3-(2-Aminoethoxyimino)-2-methyl-1-propenyl]-5β-androstane-3α,14β-diol (I-bc)

The title compound (I-bc) (0.30 g) was obtained as a fumarate, white solid, starting from (E)-3α,14β-dihydroxy-21-methyl-5β-pregn-20-ene-21-carboxaldehyde (Prepn. 8) (0.40 g) and 2-aminoethoxyamine dihydrochloride using the same procedure described in Ex. 6.

$^1$H-NMR (300 MHz, CD$_3$OD, ppm from TMS): 0.86 (3H, s); 0.98 (3H, s); 1.67 (3H, d); 2.65–2.75 (1H, m); 3.22 (2H, m); 3.75 (1H, m); 4.23 (2H, m); 6.04 (1H, dq); 6.70 (2H, s); 7.77 (1H, s).

EXAMPLE 30

(E,E)-3α-[2-(1-Pyrrolidinyl)ethoxy]-17β-[3-(2-aminoethoxyimino)-2-methyl-1-propenyl-5β-androstane-14β-ol (I-bd)

The title compound (I-bd) (0.28 g) was obtained as a white solid, starting from (E)-3α-[2-(1-pyrrolidinyl)ethoxyl-21-[2-(1,3-dioxolanyl)]-21-methyl-5β-pregn-20-ene-14β-ol (Prepn. 9) (0.35 g) and 2-aminoethoxyamine dihydrochloride using the same procedure described in Ex. 20.

$^1$H-NMR (300 MHz, CD$_3$OD, ppm from TMS): 0.86 (3H, s); 0.97 (3H, s); 1.68 (3H, d); 2.65–2.75 (1H, m); 2.80–3.00 (8H, m); 3.50–3.75 (3H, m); 4.05 (2H, t); 5.98 (1H, m); 7.70 (1H, s).

EXAMPLE 31

(E,E)-3α-(3-Aminopropoxy)-17β-[3-(2-aminoethoxyimino)-2-methyl-1-propenyl]-5β-androstane-14β-ol (I-be)

The title compound (I-be) (0.28 g) was obtained as a white solid, starting from (E)-3α-(2-aminopropoxy)-21-[2-(1,3-dioxolanyl)]-21-methyl-5β-pregn-20-ene-14β-ol (Prepn. 10) (0.35 g) and 2-aminoethoxyamine dihydrochloride using the same procedure described in Ex. 20.

$^1$H-NMR (300 MHz, CD$_3$OD, ppm from TMS): 0.86 (3H, s); 0.97 (3H, s); 1.67 (3H, d); 2.60–2.80 (3H, m); 2.90 (2H, t); 3.30–3.40 (2H,m); 3.50 (1H, m); 4.05 (2H, t); 5.98 (1H, m); 7.70 (1H, s).

PREPARATION 1

(E)-3β,14β-Dihydroxy-21-methyl-5β-pregn-20-ene-21-carboxaldehyde (II-a)

To a solution of 9.60 g of ethyl (E)-3β,14β-dihydroxy-21-methyl-5β-pregn-20-ene-21-carboxylate (Boutagy J. and Thomas R., Aust. J. Pharm, Chem., 1972, NS1, 67) in 370 ml of dry tetrahydrofuran, 104 ml of 1M i-Bu$_2$AlH in hexane were added dropwise under nitrogen at −78° C. After 2 hrs the reaction was quenched with a solution of 46.0 g of sodium sulfate in 350 ml of water and stirred at room temperature for 2 hours. The mixture was then filtered through Celite and washed with methylene chloride. The organic layer was separated, dried over anhydrous sodium sulfate and evaporated to dryness to give 8.30 g of (E)-21-hydroxymethyl-21-methyl-5β-pregn-20-ene-3β,14β-diol as an off-white solid.

¹H-NMR (300 MHz, CDCl₃, ppm from TMS): 0.85 (3H, s); 0.97 (3H, s); 1.65 (3H, d); 2.45–2.55 (1H, m); 4.00 (2H, s); 4.13 (1H, m); 5.60 (1H, dq).

To a solution of 8.40 g of (E)-21-hydroxymethyl-21-methyl-5β-pregn-20-ene-3β,14β-diol in 200 ml of chloroform, 84.0 g of MnO₂ were added at room temperature. The mixture was stirred overnight and then filtered through Celite. The organic solution was evaporated to dryness to give 7.50 g of the title compound (II-a) as an off-white solid.

¹H-NMR (300 MHz, CDCl₃, ppm from TMS): 0.87 (3H, s); 0.98 (3H, s); 1.70 (3H, d); 2.75–2.85 (1H, m); 4.15 (1H, m); 6.80 (1H, dq); 9.40 (1H, s).

PREPARATION 2

(E)-3β,14β-Dihydroxy-21-ethyl-5β-pregn-20-ene-21-carboxaldehyde (II-b)

To a stirred mixture of 1.20 g of NaH (55% dispersion in mineral oil) in 100 ml of dry THF, 6.9 ml of triethyl 2-phosphonobutirrate were added dropwise while cooling with an ice bath. After 30 minutes at room temperature, a solution of 4.80 g of 3β,14β-dihydroxy-5β-androstane-17β-carboxaldehyde (Boutagy J. and Thomas R., *Aust. J. Chem.*, 1971, 24, 2723) in 50 ml of THF was added dropwise. After 2 hours the mixture was diluted with 200 ml of aqueous 5% NaH₂PO₄ solution; the organic layer was separated and the aqueous phase was extracted with ethyl acetate. The combined organic layers were dried over anhydrous sodium sulfate and evaporated to dryness. The residue was purified by flash chromatography (SiO₂) using cyclohexane/ethyl acetate 1/1 as the eluant. The fractions containing the pure compound were collected and evaporated to dryness to give 4.70 g of ethyl (E)-3β,14β-dihydroxy-21-ethyl-5β-pregn-20-ene-21-carboxylate as an off-white solid.

¹H-NMR (300 MHz, CDCl₃, ppm from TMS): 0.85 (3H, s); 0.95 (3H, s); 2.55–2.65 (1H, m); 4.10 (1H, s); 4.15 (2H, q); 6.98 (1H, m).

From 4.50 g of (E)-3β,14β-dihydroxy-21-ethyl-5β-pregn-20-ene-1-carboxylate, following the same reaction sequence described in the Preparation 1, were obtained 3.10 g of the title compound (II-b) as an off-white solid.

¹H-NMR (300 MHz, CDCl₃, ppm from TMS): 0.87 (3H, s); 0.98 (3H, s); 2.75–2.85 (1H, m); 4.15 (1H, m); 6.80 (1H, m); 9.40 (1H, s).

PREPARATION 3

(E)-3β,14β,17β-Trihydroxy-21-methyl-5β-pregn-20-ene-21-carboxaldehyde (II-c)

To a solution of 1.35 g of ethyl (E)-3β,14β-dihydroxy-21-methyl-5β-pregn-20-ene-21-carboxylate (Boutagy J. and Thomas R., *Aust. J. Pharm. Sci.* 1972, NS1, 67) in 20 ml of dioxane, 1.10 g of selenium dioxide were added under nitrogen. The mixture was refluxed for 4 hrs, kept at room temperature overnight and then filtered. The solvent was removed under reduced pressure. Water was added to the crude product and the mixture was filtered to give 1.10 g of ethyl (E)-3β,14β, 17α-trihydroxy-21-methyl-5β-pregn-20-ene-21-carboxylate as a pale yellow solid.

¹H-NMR (300 MHz, CDCl₃, ppm from TMS): 0.80 (3H, s); 0.92 (3H, s); 1.80 (3H, d); 4.10 (1H, s); 4.15 (2H, q); 5.95 (1H, m).

1.05 g of methyl (E)-3β,14β,17α-trihydroxy-5β-pregn-20-ene-21-carboxylate were reacted first with i-Bu₂AlH and then with MnO₂, following the procedure described in Prepn. 1, to give 0.80 g of the title compound (II-c) as a pale yellow solid.

¹H-NMR (300 MHz, CDCl₃, ppm from TMS): 0.70 (3H, s); 0.90 (3H, s); 1.70 (3H, d); 3.90 (1H, m); 7.60 (1H, m); 9.50 (1H, d).

PREPARATION 4

(E)-3β-[2-(1-Pyrrolidinyl)ethoxy-21-[2-(1,3-dioxolanyl)]-21-methyl-5β-pregn-20-ene-14β-ol (II-d)

A mixture of 2.50 g of (E)-3β,14β-dihydroxy-21-methyl-5β-pregn-20-ene-21-carboxaldehyde (Prepn. 1), 11.0 ml of ethylene glycol, 50 ml of 2,2-dimethyl-1,3-dioxolane and 0.06 g of oxalic acid was heated at 40° C. for 3 days. After cooling the mixture was diluted with 5% aqueous sodium hydrogencarbonate and extracted with ethyl acetate. The organic layer was dried over anhydrous sodium sulfate and evaporated to dryness to give 2.60 g of (E)-21-[2-(1,3-dioxolanyl)]-21-methyl-5β-pregn-20-ene-3β,14β-diol as a white solid.

¹H-NMR (300 MHz, CDCl₃, ppm from TMS): 0.85 (3H, s); 0.95 (3H, s); 1.65 (3H, s); 3.85–4.05 (4H, m); 4.12 (1H, m); 5.10 (1H, m); 5.40 (1H, dd).

A mixture of 2.55 g of (E)-21-[2-(1,3-dioxolanyl)]-21-methyl-5β-pregn-20-ene-3β,14β-diol, 15.0 g of 1-(2-chloroethyl)pyrrolidine and 5.00 g of sodium hydride (55% dispersion in mineral oil) in 280 ml of dry tetrahydrofuran was refluxed for 12 hrs. After cooling, water was added and the mixture was extracted with ethyl acetate; the organic layer was dried over anhydrous sodium sulfate and evaporated to dryness. The crude product was purified by flash-chromatography (SiO₂) using chloroform/methanol 95/5 as the eluant; the fractions containing the title compound were collected and evaporated to give 1.60 g of the title compound (II-d) as a dense oil.

¹H-NMR (300 MHz, CDCl₃, ppm from TMS): 0.85 (3H, s); 1.00 (3H, s); 1.65 (3H, s); 2.85 (6H, m); 3.65 (3H, m); 3.85–4.05 (4H, m); 5.15 (1H, m); 5.40 (1H, m).

PREPARATION 5

(E)-3β-(3-(1-Pyrrolidinyl)propoxy-21-[2-(1,3-dioxolanyl)]-21-methyl-5β-pregn-20-ene-14β-ol (II-e)

The title compound (II-e) (1.10 g) was obtained as a dense oil starting from 2.10 g of (E)-21-[2-(1,3-dioxolanyl)]-21-methyl-5β-pregn-20-ene-3β,14β-diol (see Prepn. 4) and 8.00 g of 1-(3-chloropropyl)pyrrolidine using the same procedure described in Prepn. 4.

¹H-NMR (300 MHz, CDCl₃, ppm from TMS): 0.85 (3H, s); 1.00 (3H, s); 1.65 (3H, s); 2.55 (6H, m); 3.42 (2H, t); 3.62 (1H, m); 3.85–4.05 (4H, m); 5.15 (1H, m); 5.40 (1H, dd).

PREPARATION 6

(E)-3β-(2-Aminoethoxy)-21-[2-(1,3-dioxolanyl)]-21-methyl-5β-pregn-20-ene-14β-ol (II-f)

To a suspension of 7.05 g of NaH (60 % dispersion in mineral oil) in 500 ml of dry tetrahydrofuran, 8.05 g of (E)-21-[2-(1,3-dioxolanyl)]-21-methyl-5β-pregn-20-ene-3β,14β-diol (see Prepn. 4) were added at room temperature under a nitrogen atmosphere. The mixture was stirred at reflux for 7 hrs, then 35 ml of bromoacetaldehyde diethylacetal were added and the suspension was stirred at reflux for 4 hrs. After cooling at room temperature 80 ml of water were added cautiously, and tetrahydrofuran was distilled under reduced pressure. The residue was extracted with methylene chloride, the organic layer was dried over anhydrous sodium sulfate and evaporated to dryness. The crude product was purified by flash-chromatography (SiO₂) using n-hexane/ethyl acetate 75/25 as the eluant to give 9.05 g of (E)-3β-(2,2-diethoxyethoxy)-21-[2-(1,3-dioxolanyl)]-21-methyl-5β-pregn-20-ene-14β-ol, as a dense oil.

¹H-NMR (300 MHz, CDCl₃, ppm from TMS): 0.85 (3H, s); 1.00 (3H, s); 1.23 (6H, t); 1.65 (3H, s); 3.45–3.50 (2H, m); 3.50–3.80 (5H, m); 3.85–4.05 (4H, m); 4.63 (1H, t); 5.15 (1H, m); 5.40 (1H, m).

A solution of 9.00 g of 3β-(2,2-diethoxyethoxy)-17β-[2-(1,3-dioxolanyl)]-5β-androstan-14β-ol, in 720 ml of dioxane and 550 ml of a saturated aqueous solution of tartaric acid was heated at 70° C. for 2 hrs in a nitrogen atmosphere. After cooling at room temperature, 300 ml of water were added and the mixture was extracted with methylene chloride. The organic layer was washed with water, dried over anhydrous sodium sulfate and evaporated to dryness. The crude product was purified by flash-chromatography (SiO₂) using n-hexane/ethyl acetate 65/35 as the eluant to give 6.05 g of (E)-3β-formylmethoxy-21-[2-(1,3-dioxolanyl)]-21-methyl-5β-pregn-20-ene-14β-ol as a white waxy solid.

¹H NMR: (300 MHz, CDCl₃, ppm from TMS): 0.85 (3H, s); 1.02 (3H, s); 1.65 (3H, s); 3.70 (1H, bs); 3.85–4.05 (4H, m); 4.10 (2H, d); 5.15 (1H, m); 5.40 (1H, m); 9.75 (1H, t).

To a solution of 3.00 g of (E)-3β-formylmethoxy-21-[2-(1,3-dioxolanyl)]-21-methyl-5β-pregn-20-ene-14β-ol in 300 ml of methanol, 1.00 g of sodium borohydride was added slowly at 0° C. After 30 min. the temperature of the mixture was allowed to warm to 25° C. After 2 hrs. 60 ml of water were added, methanol was distilled under reduced pressure, and the residue was extracted with methylene chloride; the organic layer was washed with water, dried over sodium sulfate and evaporated to dryness. The crude product was purified by flash-chromatography (SiO₂) using n-hexane/ethyl acetate 75/25 as the eluant to give 2.25 g of (E)-3β-(2-hydroxyethoxy)-21-[2-(1,3-dioxolanyl)]-21-methyl-5β-pregn-20-ene-14β-ol as a white solid.

¹H NMR (300 MHz, CDCl₃, ppm from TMS): 0.85 (3H, s); 1.00 (3H, s); 1.65 (3H, s); 3.50 (2H, t); 3.60 (1H, bs); 3.70 (2H, t); 3.85–4.05 (4H, m); 5.15 (1H, m); 5.40 (1H, m).

A solution of 0.85 ml of diethyl azodicarboxylate was added dropwise, under nitrogen, to a stirred solution of 2.20 g of (E)-3β-(2-hydroxyethoxy)-21-[2-(1,3-dioxolanyl)]-21-methyl-5β-pregn-20-ene-14β-ol, 0.90 g of phthalimide and 1.50 g of triphenylphosphine in 23 ml of tetrahydrofuran at room temperature. After 2 hrs the solvent was evaporated to dryness. The crude product was purified by flash-chromatography (SiO₂) using n-hexane/ethyl acetate 75/25 as the eluant to give 2.40 g of (E)-3β-(2-phthalimidoethoxy)-21-[2-(1,3-dioxolanyl)]-21-methyl-5β-pregn-20-ene-14β-ol.

¹H NMR (300 MHz, CDCl₃, ppm from TMS): 0.85 (3H, s); 1.00 (3H, s); 1.65 (3H, s); 3.60–3.70 (3H, m); 3.85–4.20 (6H, m); 5.15 (1H, m); 5.40 (1H, m); 7.70–7.75 (2H, m); 7.80–7.90 (2H, m).

To a solution of 2.30 g of 3β-(2-phthalimidoethoxy)-17β-[2-(1,3-dioxolanyl)]-21-methyl-5β-androstan-14β-ol in 80 ml of ethanol (96%) 0.75 ml of hydrazine hydrate were added at room temperature. The mixture was stirred at reflux for 4 hrs, then 20 ml of water were added and the ethanol distilled under reduced pressure. The residue was extracted with methylene chloride; the organic solution was washed with water, dried over anhydrous sodium sulfate and evaporated to dryness under reduced pressure. The crude residue was purified by flash-chromatography using methylene chloride/methanol 90/10 as the eluant to give 1.05 g of the title compound (II-f) as a white solid.

¹H NMR: (300 MHz, CDCl₃, ppm from TMS): 0.85 (3H, s); 1.00 (3H, s); 1.65 (3H, s); 2.85 (2H, t); 3.40 (2H, m); 3.65 (1H, bs); 3.85–4.05 (4H, m); 5.15 (1H, m); 5.40 (1H, m).

PREPARATION 7

(E)-3β-(3-Aminopropoxy)-21-[2-(1,3-dioxolanyl)]-21-methyl-5β-pregn-20-ene-14β-ol A solution of 6.00 g of 3β,14β-dihydroxy-5β-androstane-17β-carboxaldehyde (Boutagy J. and Thomas R., Aust. J. Chem. 1971, 24, 2723), 1.20 g of oxalic acid and 20.0 ml of ethylene glycol in 140 ml of acetonitrile was stirred at room temperature for 24 hrs. After basifying with an aqueous sodium hydrogencarbonate solution the mixture was extracted with ethyl acetate; the organic layer was dried over anhydrous sodium sulfate and evaporated to dryness to give 6.10 g of 17β-(2-(1,3-dioxolanyl))-5β-androstane-3β,14β-diol as a dense oil.

¹H-NMR (300 MHz, CDCl₃, ppm from TMS): 0.98 (3H,s); 1.05 (3H, s); 3.80–4.20 (5H, m); 4.98 (1H, d).

To a solution of 6.05 g of 17β-12-(1,3-dioxolanyl)]-5β-androstan-3β,14β-diol in 80 ml of dry tetrahydrofuran. 5.80 g of sodium hydride (60% dispersion in mineral oil) were added under nitrogen atmosphere at room temperature and the resulting mixture was stirred at reflux temperature for 6 hrs. Alter cooling. 18.0 g of allyl bromide were added and the reflux continued for further 20 hrs. The mixture was quenched with water and the organic solvent was distilled under reduced pressure. The residue was extracted with ethyl acetate; the organic solution was dried over anhydrous sodium sulfate and evaporated to dryness. The residue was purified by flash-chromatography using n-hexane/ethyl acetate 80/20 as the eluant to give 5.20 g of 3β-prop-(2-en) oxy-17β-(1,3-dioxolanyl)]-5β-androstan-14β-ol as a white solid.

¹H-NMR (300 MHz, CDCl₃, ppm from TMS): 0.97 (3H, s); 1.04 (3H, s); 3.69 (1H, bs); 3.80–4.20 (6H, m); 4.99 (1H, d); 5.12–5.18 (1H, m); 5.22–5.32 (1H, m); 5.87–6.01 (1H, m).

To a solution of 5.10 g of 9-borabicyclo[3.3.1]nonane in 350 ml of dry tetrahydrofuran, 6.80 g of 3β-prop-(2-en)oxy-17β-(2-(1,3-dioxolanyl))-5β-androstan-14β-ol in 140 ml of tetrahydrofuran were added under nitrogen atmosphere, at room temperature. After stirring for 6 hrs, 12 ml of ethanol, 4.0 ml of 6N sodium hydroxide and 7 ml of 30% hydrogen peroxide were added. The mixture was stirred at 50° C. for 1 hr, quenched with a solution of 9.05 g of potassium carbonate in 200 ml of water and the organic solvent distilled under reduced pressure. The residue was extracted with methylene chloride, the organic solution was dried over anhydrous sodium sulfate and evaporated to dryness. The residue was purified by flash-chromatography using n-hexane/ethyl acetate 70/30 as the eluant to give 4.35 g of 3β-(3-hydroxypropoxy)-17β-[2-(1,3-dioxolanyl)l-5β-androstan-14β-ol as a white solid.

¹H-NMR (300 MHz, CDCl₃, ppm from TMS): 0.96 (3H, s); 1.05 (3H, s); 3.57–3.67 (3H, m); 3.80–4.20 (6H, m); 4.98 (1H, d).

A solution of 4.30 g of 3β-(3-hydroxypropoxy)-17β-[2-(1,3-dioxolanyl)]-5β-androstan-14β-ol in 100 ml of dioxane was acidified to pH 2.0 with 0.1N hydrochloric acid and stirred for 2 hours. The solution was poured into 5% aqueous sodium hydrogencarbonate and extracted with ethyl acetate. The organic layer was dried over anhydrous sodium sulfate and evaporated to dryness to give 3.50 g of 3β-(3-hydroxypropoxy)-14β-hydroxy-5β-androstan-17β-carboxaldehyde as a white solid.

¹H-NMR (300 MHz, CDCl₃, ppm from TMS): 0.96 (3H, s); 1.05 (3H, s); 3.55–3.65 (3H, m); 3.80–4.20 (2H, m); 9.25 (1H, d).

3.45 g of 3β-(3-hydroxypropoxy)-14β-hydroxy-5[β-androstan-17β-carboxaldehyde were reacted with triethyl 2-phosphonopropionate in the presence of sodium hydride, using the same procedure described in Prepn. 2, to give 3.05 g of ethyl (E)-3β-(3-hydroxypropoxy)-14β-hydroxy-21-methyl-5β-pregn-20-ene-21-carboxylate as a white foam.

$^1$H-NMR (300 MHz, CDCl$_3$, ppm from TMS): 0.85 (3H, s); 0.95 (3H, s); 1.70 (3H, s); 3.55–3.65 (3H, m); 4.15 (2H, t); 4.00–4.20 (4H, m); 7.00 (1H, dd).

3.00 g of ethyl (E)-3β-(3-hydroxypropoxy)-14β-dihydroxy-21-methyl-5β-pregn-20-ene-21-carboxylate were reacted with t-Bu$_2$AlH and successively with MnO$_2$ as described in Prepn. 1, to give 2.85 g of (E)-3β-(3-hydroxypropoxy)-14β-dihydroxy-5β-pregn-20-ene-21-carboxaldehyde.

$^1$H-NMR (300 MHz, CDCl$_3$, ppm from TMS): 0.85 (3H, s); 0.95 (3H, s); 1.70 (3H, d); 3.55–3.65 (3H, m); 4.00–4.20 (2H, m); 5.80 (1H, m); 9.40 (1H, d).

2.80 g of (E)-3β-(3-hydroxypropoxy)-14β-dihydroxy-5β-pregn-20-ene-21-carboxaldehyde were reacted with ethylene glycol, as described in Prepn. 4, to give 3.10 of (E)-3β-(3-hydroxypropoxy)-21-[2-(1,3-dioxolanyl)]-21-methyl-5β-pregn-20-ene-14β-ol as a white foam $^1$H-NMR (300 MHz, CDCl$_3$, ppm from TMS): 0.90 (3H, s); 0.95 (3H, s); 1.70 (3H, d); 3.55–3.65 (3H, m); 4.00–4.20 (2H, m); 5.20 (1H, d); 5:60 (1H, m).

0.35 ml of diethyl azodicarboxylate were added dropwise, under nitrogen, to a solution of 3.00 g of (E)-3β-(3-hydroxypropoxy)-21-[2-(1,3-dioxolanyl)]-21-methyl-5β-pregn-20-ene-14β-ol, 1.55 g of phthalimide and 3.60 g of triphenylphosphine in 55 ml of tetrahydrofuran at room temperature. After 2 hrs the solvent was removed in vacuo, the crude product was dried over anhydrous sodium sulfate and evaporated to dryness. The crude product was purified by flash-chromatography (SiO$_2$) using n-hexane/ethyl acetate 80/20 to give 3.50 g of (E)-3β-(3-phthalimidopropoxy)-21-[2-(1,3-dioxolanyl)]-21-methyl-5β-pregn-20-ene-14β-ol as a white solid.

$^1$H-NMR (300 MHz, CDCl$_3$, ppm from TMS): 0.85 (3H, s); 0.95 (3H, s); 1.70 (3H, d); 3.40–3.55 (3H, m); 3.80–4.20 (6H, m); 5.20 (1H, d); 5.60 (1H, m); 7.68–7.75 (2H, m); 7.80–7.90 (2H, m).

To a solution of 3.40 g of (E)-3β-(3-phthalimidopropoxy)-21-[2-(1,3-dioxolanyl)]-21-methyl-5β-pregn-20-ene-14β-ol in 350 ml of ethanol (96%) 2.30 g of hydrazine hydrate were added at room temperature. The mixture was stirred at reflux for 4 hrs. After cooling 10 ml of water were added and the ethanol distilled under reduced pressure. The residue was extracted with methylene chloride, the organic solution was washed with water, dried over anhydrous sodium sulfate and evaporated to dryness. The crude residue was purified by flash-chromatography (SiO$_2$) using methylene chloride/methanol 90/10 as eluant to give 1.20 g of the title compound (II-g) as a white solid.

$^1$H-NMR (300 MHz, CDCl$_3$, ppm from TMS): 0.85 (3H, s); 1.00 (3H, s); 1.70 (3H, d); 2.60–2.80 (2H, m); 3.30–3.40 (2H, m); 3.60 (1H, bs); 3.85–4.05 (4H, m); 5.20 (1H, d); 5.60 (1H, m).

PREPARATION 8

(E)-3β,14β-Dihydroxy-21-methyl-5β-pregn-20-ene-21-carboxaldehyde (II-h)

To a solution of 1.55 g (E)-21-[2-(1,3-dioxolanyl)]-21-methyl-5β-pregn-20-ene-3β,4β-diol (see Prepn. 4) in 20 ml of methylene chloride, 0.95 g of 4-methylmorpholine N-oxide, 0.15 g of tetrapropylammonium perruthenate and 1.20 g of powdered 4 Å molecular sieves were added at room temperature. After 3 hours the solvent was evaporated to dryness and the crude product purified by flash-chromatography (SiO$_2$) using n-hexane/ethyl acetate 60/40 as the eluant to give 1.35 g of (E)-21-[2-(1,3-dioxolanyl)]-5β-pregn-20-ene-14β-ol-3-one as a white solid.

$^1$H-NMR (300 MHz, CDCl$_3$, ppm from TMS): 0.85 (3H, s); 0.95 (3H, s); 1.65 (3H, s); 2.70 (1H, t); 2.80 (1H, dd); 3.85–4.05 (4H, m); 5.10 (1H, m); 5.40 (1H, m).

To a solution of 1.30 g of (E)-21-[2-(1,3-dioxolanyl)]-21-methyl-5β-pregn-20-ene-14β-ol-3-one in 15 ml of dry, tetrahydrofuran at −78° C. a solution of 3.10 g of tri-tert-butoxyaluminum hydride in 30 ml of dry tetrahydrofuran was added dropwise. The mixture was stirred for 20 hours, then 15 ml of water were added and the temperature was allowed to rise to 25° C. The mixture was filtered through Celite and the insoluble washed with methanol. The solution was concentrated under reduced pressure and extracted with methylene chloride. The organic layer was dried over sodium sulfate and evaporated to give 1.40 g of (E)-21-[2-(1,3-dioxolanyl)]-21-methyl-5β-pregn-20-ene-3α,14β-diol as a white solid.

$^1$H-NMR (300 MHz, CDCl$_3$, ppm from TMS): 0.85 (3H, s); 0.95 (3H, s); 1.65 (3H, s); 3.70 (1H, m); 3.85–4.05 (4H, m); 5.10 (1H, m); 5.40 (1H, m).

A solution of 1.35 g of (E)-21-[2-(1,3-dioxolanyl)]-21-methyl-5β-pregn-20-ene-3α,14β-diol in 15 ml of dioxane was acidified to pH 2.0 with 0.1N hydrochloric acid and stirred for 2 hours. The solution was poured into a 5% aqueous sodium hydrogencarbonate solution and extracted with ethyl acetate. The organic layer was dried over anhydrous sodium sulfate and evaporated to dryness to give 1.10 g of (E)-3α,14β-dihydroxy-21-methyl-5β-pregn-20-ene-21-carboxaldehyde (II-h) as a white solid.

$^1$H-NMR-(300 MHz, CDCl$_3$, ppm from TMS): 0.85 (3H, s); 0.95 (3H, s); 1.70 (3H, d); 2.80 (1H, m); 3.75 (1H, m); 6.80 (1H, dq); 9.40 (1H, d).

PREPARATION 9

(E)-3α-[2-(1-Pyrrolidinyl)ethoxy]-21-[2-(1,3-dioxolanyl)]-21-methyl-5β-pregn-20-ene-14β-ol (II-i)

The title compound (II-i) (0.50 g) was obtained as a white foam starting from 0.60 g of (E)-21-[2-(1,3-dioxolanyl)l-21-methyl-5β-pregn-20-ene-3β,14β-diol (see Prepn. 8) using the same procedure described in Prepn. 4.

$^1$H-NMR (300 MHz, CDCl$_3$, ppm from TMS): 0.85 (3H, s); 0.95 (3H, s); 1.65 (3H, s); 2.85 (6H, m); 3.60 (3H, m); 3.85–4.05 (4H, m); 5.10 (1H, m); 5.40 (1H, dd).

PREPARATION 10

(E)-3β-(2-Aminoethoxy)-21-[2-(1,3-dioxolanyl)]-21-methyl-5β-pregn-20-ene-14β-ol (II-j)

The title compound (II-j) (0.80 g) was obtained as a white foam starting from 4.50 g of (E)-21-[2-(1,3-dioxolanyl) 1-21-methyl-5β-pregn-20-ene-3α,14β-diol (see Prepn. 8) using the same procedure described in Prepn. 6.

$^1$H NMR: (300 MHz, CDCl$_3$, ppm from TMS): 0.85 (3H, s); 1.00 (3H, s); 1.65 (3H, s); 2.85 (2H, t); 3.40 (2H, m); 3.55 (1H, bs); 3.85–4.05 (4H, m); 5.15 (1H, m); 5.40 (1H, m).

Compounds of general formula (I) prepared according to the invention and their pharmaceutically acceptable salts are useful agents for the treatment of cardiovascular disorders such as heart failure and hypertension.

Compounds of general formula (I) prepared according to the invention and their pharmaceutically acceptable salts have reduced toxicity, compared to known positive inotropic agents such as ouabain and digitoxin.

Moreover said compounds (I) show good affinity for the receptor site of the $Na^+,K^+$-ATPase and good inhibition of the said enzyme.

To test the affinity for the receptor site of the $Na^+,K^+$-ATPase and the agonist or antagonist activity on the enzyme, the following tests were used:

a) displacement of the specific $^3H$-ouabain binding from the $Na^+,K^+$-ATPase receptor purified according to Jorghensen (Jorghensen P., BBA. 1974, 356, 36) and Erdmann (Erdmann E. et al., *Arzneim. Forsh.*, 1984, 34, 1314);

b) inhibition of the activity of the purified $Na^+,K^+$-ATPase measured as % of hydrolysis of $^{32}P$-ATP in presence and in absence of the tested compound (Doucet A. et al. *Am. J. Physiol.*, 1986, 251, F851)

Systolic blood pressure (SBP) and heart rate (HR) were measured. by the tail cuff method, in young prehypertensive male rats (MHS or SHR) strains before the development of hypertension (4 weeks of age) for recording the basal values of SBP. Groups of 7 rats were formed and subdivided in control and treated groups. The compound, suspended in Methocel 0.5 % (w/v). was orally given daily for at least 5 weeks to the treated groups. The control group received only Methocel.

SBP and HR were measured weekly 6 and 24 hrs after treatment. After 5 weeks of treatment, when hypertension was fully developed in the control group (9 weeks of age), washout was started for at least one week, to verify whether the treatment maintained blood pressure low or reestablished the basal values. The validity of this procedure for detecting an hypotensive activity, had been previously tested for β blockers, which did not produce any hypotensive effect when acutely given to hypertensive rats (SHR), but were effective in preventing the development of hypertension when administered starting from weaning for more than 5 weeks. (Takeda K. et al., *Japan J. Pharmacol.*, 1979, 29,171: Takeda K. et al. *Japan J. Pharmacol.*, 1982, 32, 283; Richer C. et al. *Eur. J. Pharmacol.*, 1978, 47,393).

The affinity and the inhibitory activity of some compounds in the two tests are shown in the following table:

| | Binding $^3H$-Ouab. Displacement -log $IC_{50}$ | Inhibitory Activity -log $IC_{50}$ |
|---|---|---|
| Comp. I-aa | 7.5 | 6.6 |
| Comp. I-ab | 7.2 | 5.5 |
| Comp. I-ac | 6.5 | 5.4 |
| Comp. I-ad | 7.2 | 5.6 |
| Comp. I-ae | 6.3 | 5.2 |
| Comp. I-af | 7.7 | 7.5 |
| Comp. I-ag | 7.6 | 7.3 |
| Comp. I-ah | 7.7 | 7.2 |
| Comp. I-ai | 7.5 | 7.2 |
| Comp. I-aj | 7.3 | 6.9 |
| Comp. I-ak | 7.2 | 6.7 |
| Comp. I-al | 6.9 | 6.0 |
| Comp. I-am | 7.2 | 6.9 |
| Comp. I-an | 7.0 | 6.5 |
| Comp. I-ao | 6.9 | 6.3 |
| Comp. I-ap | 6.7 | 6.2 |
| Comp. I-aq | 6.4 | 5.4 |
| Comp. I-ar | 6.5 | 5.6 |
| Comp. I-as | 6.4 | 5.5 |
| Comp. I-at | 7.4 | 6.8 |

-continued

| | Binding $^3H$-Ouab. Displacement -log $IC_{50}$ | Inhibitory Activity -log $IC_{50}$ |
|---|---|---|
| Comp. I-au | 7.7 | 7.4 |
| Comp. I-av | 7.3 | 6.7 |
| Comp. I-aw | 7.6 | 7.2 |
| Comp. I-az | 7.6 | 7.4 |
| Comp. I-ay | 7.6 | 7.5 |
| Comp. I-az | 7.6 | 7.5 |
| Comp. I-ba | 7.7 | 7.4 |
| Comp. I-bb | 6.2 | 5.5 |
| Comp. I-bc | 6.3 | 5.6 |
| Comp. I-bd | 6.3 | 5.5 |
| Comp. I-be | 6.2 | 5.4 |

The activity of some new compound in preventing the development of hypertension is shown in the following table:

| EFFECT OF 5 WEEK-TREATMENT IN SPONTANEOUS HYPERTENSIVE RATS (MHS) ON THE DEVELOPMENT OF HYPERTENSION | | | | |
|---|---|---|---|---|
| Compound | RATS | DOSE* mg/Kg/os | SBP mm Hg | HR beats/min. |
| Controls | 7 | Methocel | 171 +/– 4.5 | 375 +/– 7.3 |
| Comp. I-aa | 7 | 10 | 148 +/– 5.7 | 374 +/– 9.5 |
| Comp. I-af | 7 | 10 | 146 +/– 6.1 | 380 +/– 3.9 |

*in Methocel 0.5% w/v

We claim:

1. Stereoisomers, Z and E isomers and their mixtures, optical isomers and mixtures thereof and pharmaceutically acceptable salts of compounds of general formula (I):

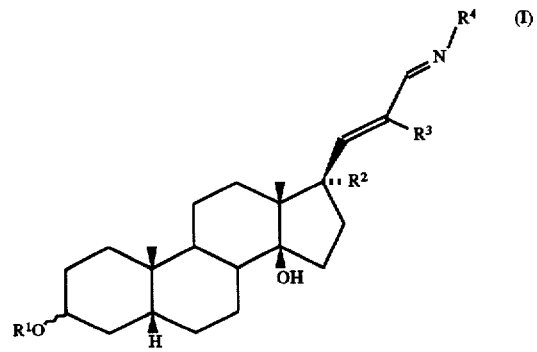

wherein:

the symbol ⁓ means α or β configuration;

the double bonds are in the E configuration;

$R^1$ represents hydrogen, C2–C4 alkyl unsubstituted or substituted by $NR^5R^6$ wherein $R^5$ and $R^6$, which may be the same or different, represent hydrogen, C1–C4 alkyl, or $R^5$ and $R^6$, taken together with the nitrogen atom they are linked to, form a five- or six-membered saturated heterocyclic ring optionally containing one or more additional heteroatoms selected from oxygen and nitrogen;

$R^2$ represents hydrogen or hydroxy;

$R^3$ represents methyl, ethyl or n-propyl; and $R^4$ represents $NHC(=N-R^7)NR^8R^9$ or $OR^{10}$ wherein $R^7$ represents hydrogen, methyl or C2–C4 alkyl, where the C2–C4 alkyl is unsubstituted or substituted by NR$^5$R$^6$, wherein R$^5$ and R$^6$ have the previously defined meanings;

R$^8$ and R$^9$, which may be the same or different, represent hydrogen, methyl or C2–C4 alkyl, where the C2–C4 alkyl is unsubstituted or substituted by NR$^5$R$^6$, wherein R$^5$ and R$^6$ have the previously defined meanings;

R$^{10}$ represents hydrogen, methyl or C2–C4 alkyl, where the C2–C4 alkyl is unsubstituted or substituted by one or more NR$^5$R$^6$ or NHC(=NH)NH$_2$, wherein R$^5$ and R$^6$ have the previously defined meanings;

the symbol ⁓ means Z or E configuration; or two of R$^7$, R$^8$, and R$^9$, taken together with the heteroatoms they are linked to, form a five- or six- or seven-membered heterocyclic ring.

2. A pharmaceutical composition, comprising the compound of claim 1 and pharmaceutically acceptable carrier or diluent.

3. A method of inhibiting a Na$^+$,K$^+$-ATPase, comprising administering to a patient in need thereof an effective amount of the compound of claim 1.

4. A method of treating hypertension, comprising administering to a patient in need thereof an effective amount of the compound of claim 1.

5. An 17-(3-[I]imino-2-alkylpropenyl)-14β-hydroxy-5β-androstane derivative of general formula (I):

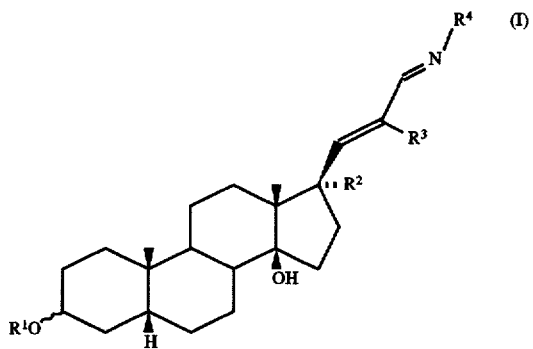

wherein:

the symbol ⁓ means α or β configuration;

the double bonds are in the E configuration;

R$^1$ represents hydrogen, C2–C4 alkyl unsubstituted or substituted by NR$^5$R$^6$ wherein R$^5$ and R$^6$, which may be the same or different, represent hydrogen, C1–C4 alkyl, or R$^5$ and R$^6$, taken together with the nitrogen atom they are linked to, form a five- or six-membered saturated heterocyclic ring optionally containing one or more additional heteroatoms selected from oxygen and nitrogen;

R$^2$ represents hydrogen or hydroxy;

R$^3$ represents methyl, ethyl or n-propyl; and

R$^4$ represents NHC(=N⁓R$^7$)NR$^8$R$^9$ or OR$^{10}$ wherein

R$^7$ represents hydrogen, methyl or C2–C4 alkyl, where the C2–C4 alkyl is unsubstituted or substituted by NR$^5$R$^6$, wherein R$^5$ and R$^6$ have the previously defined meanings;

R$^8$ and R$^9$, which may be the same or different, represent hydrogen, methyl or C2–C4 alkyl, where the C2–C4 alkyl is unsubstituted or substituted by NR$^5$R$^6$, wherein R$^5$ and R$^6$ have the previously defined meanings;

R$^{10}$ represents hydrogen, methyl or C2–C4 alkyl, where the C2–C4 alkyl is unsubstituted or substituted by one or more NR$^5$R$^6$ or NHC(=NH)NH$_2$, wherein R$^5$ and R$^6$ have the previously defined meanings;

the symbol ⁓ means Z or E configuration; or two of R$^7$, R$^8$, and R$^9$, taken together with the heteroatoms they are linked to, form a five- or six- or seven-membered heterocyclic ring.

6. A compound according to claim 1, which is selected from:

(E,E)-17β-(3-guanidinoimino-2-methyl-1-propenyl)-5β-androstane-3β,14β-diol, (E,E)-17β-[3-(2-imidazolin-2-yl)hydroazono-2-methyl-1-propenyl]-5β-androstane-3β,14β-diol, (E,E)-17β-[3-(1-methyl-2-imidazolin-2-yl)hydrazono-2-methyl-1-propenyl]-5β-androstane-3β,14β-diol, (E,E)-17β-[3-(2-imidazolyl)hydrazono-2-methyl-1-propenyl]-5β-androstane-3β,14β-diol, (E,E)-17β-[3-(1,4,5,6-tetrahydro-2-pyrimidinyl)hydrazono-2-methyl-1-propenyl]5β-androstane-3β,14β-diol, (E,E)-17β-(3-[3-(2-dimethylaminoethyl)guanidinoimino]-2-methyl-1-propenyl)-5β-androstane-3β,14β-diol, (E,E)-17β-[3-(2-aminoethoxyimino)-2-methyl-1-propenyl]-5β-androstane-3β,14β-diol, (E,E)-17β-[3-(3-aminopropoxyimino)-2-methyl-1-propenyl]-5β-androstane-3β,14β-diol, (E,E)-17β-[3-(2-dimethylaminoethoxyimino)-2-methyl-1-propenyl]-5β-androstane-3β,14β-diol, (E,E)-17β-[3-(3-dimethylaminopropoxyimino)-2-methyl-1-propenyl]-5β-androstane-3β,14β-diol, (E,E)-17β-[3-(2-guanidinoethoxyimino)-2-methyl-1-propenyl]-5β-androstane-3β,14β-diol, (E,E)-17β-[3-(3-guanidinopropoxyimino)-2-methyl-1-propenyl]-5β-androstane-3β,14β-diol, (E,E)-17β-(3-guanidinoimino-2-ethyl-1-propenyl)-5β-androstane-3β,14β-diol, (E,E)-17D-[3-(2-imidazolin-2-yl)hydrazono-2-ethyl-1-propenyl]-5β-androstane-3β,14β-diol, (E,E)-17β-[3-(1,4,5,6-tetrahydro-2-pyrimidinyl)hydrazono-2-ethyl-1-propenyl]-5β-androstane-3β,14β-diol, (E,E)-17β-[3-(2-aminoethoxyimmino)-2-ethyl-1-propenyl]-5β-androstane-3β,14β-diol, (E,E)-17β-[3-(3-aminopropoxyimino)-2-ethyl-1-propenyl]-5β-androstane-3β,14β-diol, (E,E)-17β-[3-(2-dimethylammoethoxyimino)-2-ethyl-1-propenyl]-5β-androstane-3β,14β-diol, (E,E)-17β-[3-(3-dimethylaminopropoxyimino)-2-ethyl-1-propenyl]-5β-androstane-3β,14β-diol, (E,E)-17D-[3-(2-guanidinoethoxyimino)-2-ethyl-1-propenyl]5β-androstane-3β,14β-diol, (E,E)-17β-[3-(3-guanidinopropoxyimido)-2-ethyl-1-propenyl]-5β-androstane-3β,14β-diol, and the corresponding 3β-(2-aminoethyl), 3β-(2-dimethylaminoethyl), 3β-(2-(1-pyrrolidinyl)ethyl) 3β-(3-aminopropyl), 3β-(3-dimethylaminopropyl) and 3β-(3-(1-pyrrolidinyl)propyl) ethers of the compounds mentioned above;

and the corresponding 3α-hydroxy compounds of the 3β-hydroxy derivatives;

and the corresponding 3α-(2-aminoethyl), 3α-(2-dimethylaminoethyl), 3α-(2-(1-pyrrolidinyl)ethyl) 3α-(3-aminopropyl), 3α-(3-dimethylaminopropyl) and 3α-

(3-(1-pyrrolidinyl)propyl) ethers of the compounds mentioned above;

and the corresponding 17α-hydroxy compounds of the compounds mentioned above.

7. A pharmaceutical composition, comprising the compound of claim 6 and pharmaceutically acceptable carrier or diluent.

8. The compound of claim 5, wherein said C1–C4 alkyl is ethyl, n-propyl, iso-propyl, n-butyl or tert-butyl.

9. The compound of claim 5, wherein $R^1$ is hydrogen, 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl or 3-(1-pyrrolidinyl)-propyl.

10. The compound of claim 1, wherein $R^7$ is hydrogen, methyl, 2-aminoethyl, 3-aminopropyl, 2-dimethylaminoethyl, 3-dimethylaminopropyl, 2-(1-pyrrolidinyl)ethyl or 3-(1-pyrrolidinyl)propyl.

11. The compound of claim 5, wherein $R^7$ and $R^8$, taken with the heteroatoms they are linked to, form a 2-imidazolyl, 2-(1-methyl)imidazolyl, 11,4,5,6-tetrahydro-2-pyrimidinyl or 1-methyl-1,4,5,6-tetrahydro-2-pyrimidinyl group.

12. The compound of claim 5, wherein —$NR^8R^9$ is amino, methylamino, dimethylamino, diethylamino, isopropylamino, pyrrolidinyl, piperidyl, morfolino, piperazin-1-yl, 4-methylpiperazin-1-yl, 4-(2-dimethylaminoethyl)piperazin-1-yl, 2-dimethylaminoethylamino, 2-diethylaminoethylamino, (2-dimethylamionethyl)methylamino, (2-diethylamino-ethyl)methylamino, 2-(1-pyrrolidinyl)ethylamino, 3-(1-pyrrolidinyl)propylamino or (2-(1-pyrrolidinyl)ethyl)methylamino.

13. The compound of claim 5, wherein $R^{10}$ is 2-aminoethyl, 3-aminopropyl, 2-dimethylaminoethyl, 3-dimethylaminopropyl, 2-diethylaminoethyl, 3-diethylaminopropyl, 2-(1-pyrrolidinyl)ethyl, 3-(1-pyrrolidinyl)propyl, 2-guanidinoethyl or 3-guanidinopropyl.

14. A method of inhibiting a $Na^+,K^+$-ATPase, comprising administering to a patient in need thereof an effective amount of the compound of claim 5.

15. A method of inhibiting a $Na^+,K^+$-ATPase, comprising administering to a patient in need thereof an effective amount of the compound of claim 6.

16. A method of treating hypertension, comprising administering to a patient in need thereof an effective amount of the compound of claim 5.

17. A method of treating hypertension, comprising administering to a patient in need thereof an effective amount of the compound of claim 6.

18. A process, comprising condensing a compound of general formula (II);

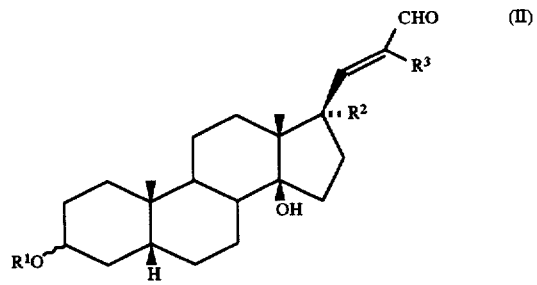

with a compound of general formula (III) or (IV):

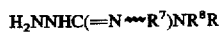   (III)

   (IV)

to produce a compound of general formula (I):

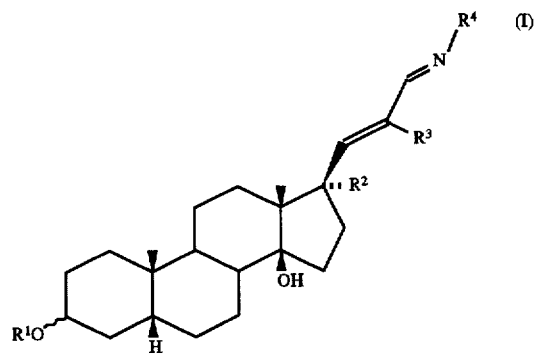

wherein:

the symbol ⁓ means α or β configuration;

the double bonds are in the E configuration;

$R^1$ represents hydrogen, C2–C4 alkyl unsubstituted or substituted by $NR^5R^6$ wherein $R^5$ and $R^6$, which may be the same or different, represent hydrogen, C1–C4 alkyl, or $R^5$ and $R^6$, taken together with the nitrogen atom they are linked to, form a five- or six-membered saturated heterocyclic ring optionally containing one or more additional heteroatoms selected from oxygen and nitrogen;

$R^2$ represents hydrogen or hydroxy;

$R^3$ represents methyl, ethyl or n-propyl; and $R^4$ represents NHC(=N⁓$R^7$)$NR^8R^9$ or $OR^{10}$ wherein $R^7$ represents hydrogen, methyl or C2–C4 alkyl, where the C2–C4 alkyl is unsubstituted or substituted by $NR^5R^6$, wherein $R^5$ and $R^6$ have the previously defined meanings;

$R^8$ and $R^9$, which may be the same or different, represent hydrogen, methyl or C2–C4 alkyl, where the C2–C4 alkyl is unsubstituted or substituted by $NR^5R^6$, wherein $R^5$ and $R^6$ have the previously defined meanings;

$R^{10}$ represents hydrogen, methyl or C2–C4 alkyl, where the C2–C4 alkyl is unsubstituted or substituted by one or more $NR^5R^6$ or $NHC(=NH)NH_2$, wherein $R^5$ and $R^6$ have the previously defined meanings;

the symbol ⁓ means Z or E configuration; or two of $R^7$, $R^8$, and $R^9$, taken together with the heteroatoms they are linked to, form a five- or six- or seven-membered heterocyclic ring.

19. A pharmaceutical composition, comprising:

(A) a compound of general formula (I):

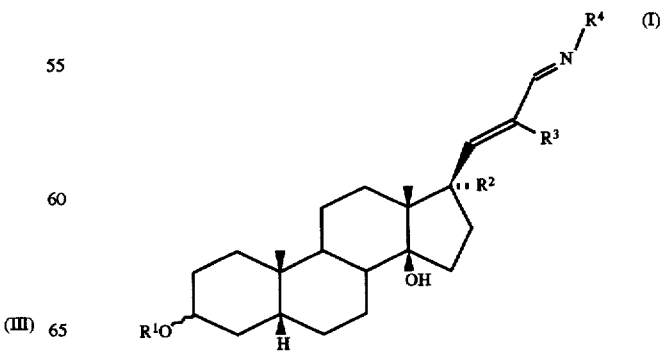

wherein:

the symbol ⌇ means α or β configuration;

the double bonds are in the E configuration;

$R^1$ represents hydrogen, C2–C4 alkyl unsubstituted or substituted by $NR^5R^6$ wherein
  $R^5$ and $R^6$, which may be the same or different, represent hydrogen, C1–C4 alkyl,
  or $R^5$ and $R^6$, taken together with the nitrogen atom they are linked to, form a five- or six-membered saturated heterocyclic ring optionally containing one or more additional heteroatoms selected from oxygen and nitrogen;

$R^2$ represents hydrogen or hydroxy;

$R^3$ represents methyl, ethyl or n-propyl; and $R^4$ represents $NHC(=N⌇R^7)NR^8R^9$ or $OR^{10}$ wherein
  $R^7$ represents hydrogen, methyl or C2–C4 alkyl, where the C2–C4 alkyl is unsubstituted or substituted by $NR^5R^6$, wherein $R^5$ and $R^6$ have the previously defined meanings;

$R^8$ and $R^9$, which may be the same or different, represent hydrogen, methyl or C2–C4 alkyl, where the C2–C4 alkyl is unsubstituted or substituted by $NR^5R^6$, wherein $R^5$ and $R^6$ have the previously defined meanings;

$R^{10}$ represents hydrogen, methyl or C2–C4 alkyl, where the C2–C4 alkyl is unsubstituted or substituted by one or more $NR^5R^6$ or $NHC(=NH)NH_2$, wherein $R^5$ and $R^6$ have the previously defined meanings;

the symbol ⌇ means Z or E configuration; or two of $R^7$, $R^8$, and $R^9$, taken together with the heteroatoms they are linked to, form a five- or six- or seven-membered heterocyclic ring; and (B) a pharmaceutically acceptable carrier or diluent.

\* \* \* \* \*